United States Patent
Suzuki et al.

(10) Patent No.: US 7,442,843 B2
(45) Date of Patent: Oct. 28, 2008

(54) PROCESS FOR PRODUCING CUMENE AND PROCESS FOR PROPYLENE OXIDE PRODUCTION INCLUDING THE PRODUCTION PROCESS

(75) Inventors: Tetsuo Suzuki, Ichihara (JP); Masaru Ishino, Sodegaura (JP); Toshio Nakayama, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/572,450

(22) PCT Filed: Sep. 15, 2004

(86) PCT No.: PCT/JP2004/013869

§ 371 (c)(1),
(2), (4) Date: Mar. 20, 2006

(87) PCT Pub. No.: WO2005/030683

PCT Pub. Date: Apr. 7, 2005

(65) Prior Publication Data

US 2006/0217566 A1  Sep. 28, 2006

(30) Foreign Application Priority Data

Sep. 25, 2003 (JP) .............................. 2003-333143

(51) Int. Cl.
*C07C 1/20* (2006.01)
*C07C 301/00* (2006.01)

(52) U.S. Cl. ........................ 585/469; 549/523; 549/525; 549/529

(58) Field of Classification Search ................. 585/469; 549/525, 523, 529
See application file for complete search history.

(56) References Cited

U.S. PATENT DOCUMENTS

| 4,075,254 A | 2/1978 | Boodman et al. |
| 5,723,637 A * | 3/1998 | Tsuji et al. .................. 549/529 |
| 6,160,137 A * | 12/2000 | Tsuji et al. .................. 549/523 |
| 2003/0032822 A1 | 2/2003 | Tsuji et al. |

FOREIGN PATENT DOCUMENTS

| EP | 1 209 155 A | 5/2002 |
| EP | 1 433 769 A1 | 6/2004 |
| GB | 1 115 186 A | 5/1968 |
| GB | 1 122 702 A | 8/1968 |
| JP | 2001-270877 A | 10/2001 |
| JP | 2001-270880 A | 10/2001 |
| JP | 2003-81886 A | 3/2003 |
| JP | 2003-818886 A | 3/2003 |

* cited by examiner

*Primary Examiner*—Sikarl A Witherspoon
(74) *Attorney, Agent, or Firm*—Sughrue Mion, PLLC

(57) ABSTRACT

A process for producing cumene by subjecting cumyl alcohol to hydrogenolysis or hydrogenation subsequent to dehydration, which comprises using a palladium-based catalyst as a catalyst for the hydrogenolysis or the hydrogenation, and using hydrogen having a carbon monoxide concentration of 0.1 to 10% by volume as hydrogen.

8 Claims, No Drawings

PROCESS FOR PRODUCING CUMENE AND PROCESS FOR PROPYLENE OXIDE PRODUCTION INCLUDING THE PRODUCTION PROCESS

TECHNICAL FIELD

The present invention relates to a process for producing cumene. More particularly, the present invention relates to a process for efficiently producing cumene from cumyl alcohol and a process for producing propylene oxide containing said process.

BACKGROUND ART

As a process for producing cumene by subjecting cumyl alcohol to hydrogenation, namely, to hydrogenolysis or dehydration-hydrogenation, it is disclosed in, for example, JP2001-270880A and 2003-081886A to convert into cumene by hydrogenolysis of cumyl alcohol with a copper-based catalyst in a hydrogenolysis step of propylene oxide production. Especially, in use of with the copper-based catalyst, cumene can be obtained under high yield since nuclear-hydrogenation of cumyl alcohol difficultly takes place in hydrogenation.

In addition, the present inventors have conducted a study on use of a palladium-based catalyst as a hydrogenation catalyst for producing cumene from cumyl alcohol under higher activity compared to the copper-based catalyst. But, though a high activity could be obtained in use of the palladium-based catalyst, there was a problem that selectivity markedly decreased because nuclear-hydrogenation of cumyl alcohol took place.

DISCLOSURE OF THE INVENTION

An object of the present invention is to provide a process for producing cumene from cumyl alcohol with a palladium-based catalyst as a hydrogenation catalyst under high activity and selectivity.

Further, another object of the present invention is to provide a process for producing propylene oxide containing the process described above.

That is, the present invention relates to a process for producing cumene by subjecting cumyl alcohol to hydrogenolysis or hydrogenation subsequent to dehydration, which comprises using a palladium-based catalyst as a catalyst for the hydrogenolysis or the hydrogenation, and using hydrogen having a carbon monoxide concentration of 0.1 to 10% by volume as hydrogen.

In addition, the present invention relates to a process for producing propylene oxide, which comprises the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene in an excess amount; and cumene production step: a step of producing cumene by subjecting cumyl alcohol obtained in the epoxidation step to hydrogenolysis or hydrogenation subsequent to dehydration and recycling said cumene to the oxidation step, and which comprises using a palladium-based catalyst as a catalyst for hydrogenolysis or hydrogenation; and using hydrogen containing 0.1 to 10% by volume of carbon monoxide as hydrogen.

BEST MODE FOR CARRYING OUT THE INVENTION

As a method for producing cumene from cumyl alcohol with a palladium-based catalyst, the following methods are shown:

Namely, a method for producing cumene by converting cumyl alcohol into α-methyl styrene by contacting with a dehydration catalyst, and then subjecting α-methyl styrene to hydrogenation by contacting with a palladium-based catalyst in the presence of hydrogen (hereinafter, sometimes referred to as "dehydration-hydrogenation"), and a method for producing cumene by contacting cumyl alcohol with a palladium-based catalyst in the presence of hydrogen to carry out hydrogenolysis.

There is explained the method of converting into α-methyl styrene by dehydrating the before-mentioned cumyl alcohol and then converting into cumene by hydrogenating said α-methyl styrene.

A catalyst used in dehydration includes acids such as sulfuric acid, phosphoric acid and p-toluene sulfonic acid and metal oxides such as activated alumina, titania, zirconia, silica-alumina and zeolites, and activated alumina is preferable from viewpoints of separation from the reaction mixture, catalyst life, selectivity, etc.

The dehydration is usually conducted by contacting cumyl alcohol with the dehydration catalyst, but, in the present invention, hydrogen may be fed together with cumyl alcohol to the dehydration catalyst to conduct the hydrogenation subsequent to the dehydration.

The reaction can be conducted in a liquid phase using a solvent. The solvent should be substantially inert to reactants and products. The solvent may be a substance present in a cumyl alcohol solution to be used. For example, when cumyl alcohol is a mixture with cumene as a product, it is possible to use cumene as a substitute without adding a solvent in particular. The dehydration temperature is usually 50 to 450° C., preferably 150 to 300° C. In usual, the pressure is advantageously 10 to 10,000 kPa. The dehydration can be advantageously conducted by using a catalyst in a slurry form or fixed-bed form. An amount of the dehydration catalyst used may be an amount enough to convert cumyl alcohol.

In the present invention, α-methyl styrene obtained in the dehydration and hydrogen are supplied to a hydrogenation catalyst for hydrogenating α-methyl styrene thereby producing cumene. As the hydrogenation catalyst, a palladium-based catalyst are used, and as the palladium-based catalyst, supported type catalyst such as palladium/alumina, palladium/silica and palladium/carbon are listed. Though a concentration of palladium is preferably low for suppressing a nuclear hydrogenation as a side reaction, the palladium concentration which is too low leads to disadvantage in reaction rate. The concentration of palladium supported is generally from 0.005 to 10% by weight, preferably 0.01 to 1% by weight.

These catalyst can be used alone or in mixture of 2 or more. An amount of the hydrogenation catalyst used may be an amount enough to convert α-methyl styrene into cumene, and the conversion of α-methyl styrene is preferably 98% or more.

As hydrogen used, it is necessary to use hydrogen having a carbon monoxide concentration of 0.1 to 10% by volume, preferably 0.5 to 5% by volume. When the concentration of carbon monoxide (herein-after, may be referred to as "CO") is less than 0.1% by volume, a selectivity of cumene markedly decrease because hydrogenation of an aromatic nuclear raises as a side reaction in the hydrogenation or hydrogenolysis, on the other hand, when over 10% by volume, it is impossible to attain the object of the present invention because the reaction activity significantly decreases.

CO may be contained in fresh hydrogen as a raw material or recycled hydrogen in the cumene producing step. When recycled hydrogen is used, the valance after which a part of an excess amount of unreacted hydrogen in the cumene producing step has been purged or the whole amount of the unreacted hydrogen without purging is recycled in the cumene producing step. CO contained in the recycled hydrogen may be that produced by hydrogenolysis of formic acid or a formic acid derivative formed mainly in the epoxidation step, or that added newly. In a case of which fresh hydrogen and the recycled hydrogen are simultaneously used, a larger ratio of recycled hydrogen containing CO leads to become advantageous in hydrogen cost because fresh hydrogen can be reduced. Further, when CO is contained in hydrogen, the nuclear hydrogenation of the aromatic ring as a side reaction in the hydrogenation or hydrogenolysis, is suppressed. Isopropyl cyclohexane, isopropyl cyclohexene and the like as products in the side reaction, are an oxidation inhibiter, and the oxidation rate and cumene hydroperoxide selectivity significantly decrease when the reaction mixture (mainly cumene) containing these products from the cumene producing step is recycled to the oxidation step. Accordingly, when CO is contained in hydrogen used in the hydrogenation/hydrogenolysis in the cumene producing step, the nuclear hydrogenation of the aromatic ring can be suppressed and therefore, it is possible to more advantageously progress the oxidation.

For the meanwhile, because CO is an inhibiting component of the hydrogenation/hydrogenolysis, when CO in hydrogen is supplied to the reaction, the activity of the palladium-based catalyst deteriorates, further when the CO concentration exceeds the above-described range, the activity decreases to an impermissible degree in the $\alpha$-methyl styrene conversion.

Therefore, it is essential to control the CO concentration in hydrogen used in the hydrogenation/hydrogenolysis within the above range taking account of the conversion of cumyl alcohol.

Cumene obtained in the cumene producing step is recycled as a raw material to the oxidation step.

Though the hydrogenation is carried out by contacting $\alpha$-methyl styrene and hydrogen with the hydrogenation catalyst, a part of water generated may be separated by oil-water separation or the like or may be supplied together with $\alpha$-methyl styrene to the hydrogenation catalyst for carrying out the hydrogenation subsequent to the dehydration.

Though the amount of hydrogen required in the reaction may be equimolar to $\alpha$-methyl styrene theoretically, an excess amount of hydrogen is required because other components which consume hydrogen are contained in the raw material.

As a molar ratio of hydrogen to $\alpha$-methyl styrene, the range of 1 to 10 is usually applied because the reaction proceeds rapidly with increase of a partial pressure of hydrogen. The range is further preferably 1 to 5. The excess amount of hydrogen remained after the reaction can be recycled after separated from the reaction mixture. The hydrogenation can be conducted in a liquid phase using a solvent or gas phase. The solvent should be substantially inert to the reactants and products. The solvent may be a substance existing in an $\alpha$-methyl styrene solution to be used. For example, when $\alpha$-methyl styrene is a mixture with cumene as a product, it is possible to use cumene as a substitute of the solvent without adding a solvent in particular. The hydrogenation temperature is usually 0 to 500° C., preferably 30 to 400° C. In usual, the pressure is advantageously 100 to 10,000 kPa.

As modes of the dehydration and hydrogenation, these reactions can be usually conducted by a continuous method using a catalyst in the form of a fix-bed. The dehydration and hydrogenation may be conducted using separate reactors or a single reactor. As a reactor used in the continuous method, there are an adiabatic reactor and an isothermal reactor, and the adiabatic reactor is preferable because the isothermal reactor requires an apparatus for removal of heat. In a case of the adiabatic reactor, the temperature lowers with progress of the reaction because the dehydration of cumyl alcohol is an endothermic reaction, and on the other hand, since the hydrogenation of $\alpha$-methyl styrene is an exothermic reaction, the temperature rises with progress of the reaction. The outlet temperature becomes higher than the inlet temperature because the generated heat quantity is larger in total.

The reaction temperature and pressure are selected so that water contained in an $\alpha$-methyl styrene solution after the dehydration, is not condensed. The reaction temperature is preferably 150 to 300° C., and the reaction pressure is preferably 100 to 2000 kPa. When the temperature is too low or the pressure is too high, water may be condensed at the outlet of the dehydration, leading to deterioration of the performance of the hydrogenation catalyst. Further, when the pressure is too high, it is also disadvantageous in the reaction equilibrium of dehydration. When the temperature is too high or the pressure is too low, it may become disadvantageous because the catalyst life is shortened by howling or the like caused by much generation of the gas phase part.

Though hydrogen can be supplied from any one of an inlet of a dehydration reactor and an inlet of a hydrogenation reactor, it is preferable to supply from the inlet of the dehydration catalyst in view of the activity of the dehydration catalyst. That is, vaporization of water produced through dehydration is promoted by bringing into constant existence of hydrogen in the dehydration zone and the equilibrium dehydration conversion rises, therefore, high conversion can be attained effectively compared to absence of hydrogen. Though water generated in the dehydration is passed through the hydrogenation catalyst, it is possible to operate at low cost without particularly setting up an apparatus for water removal as described above, by operating at the level not condensing water. Further, unreacted hydrogen in the hydrogenation can be recycled after gas-liquid separation operation.

Furthermore, at the time of the gas-liquid separation operation, it is possible to separate water generated in the dehydration from the reaction mixture. A part of the obtained reaction mixture (mainly cumene) can be recycled to the reactor for use.

Considering from a viewpoint of cost, the dehydration and hydrogenation catalysts are preferably packed in one reactor having a plurality of fixed beds but not in a plurality of reactors. Inside of the reactor may be partitioned into several beds or not. When the reactor is not partitioned, the dehydration catalyst and hydrogenation catalyst may be directly contacted each other or those may be partitioned with an inert packing.

A case of which production of cumene from cumyl alcohol is conducted by hydrogenolysis, is explained below:

The hydrogenolysis is a reaction for obtaining cumene by subjecting cumyl alcohol obtained in the epoxidation step to hydrogenolysis, and is a reaction in which dehydration and hydrogenation apparently proceed at the same time. The hydrogenolysis is carried out by contacting cumyl alcohol and hydrogen with a catalyst. As the catalyst, though the above-described palladium-based catalyst used for hydrogenation of α-methyl styrene, is used, it is possible to efficiently carry out hydrogenolysis by using a palladium-based catalyst in which palladium is supported on a carrier showing a catalyst activity in dehydration such as activated alumina, in particular.

Of course, as hydrogen used herein, hydrogen having a carbon monoxide concentration of 0.1 to 10% by volume, which is similar to that used in the hydrogenation, is used from the same reason as described above.

The hydrogenolysis can be efficiently carried out in a liquid phase using a solvent. The solvent should be substantially inert to the reactants and products. The solvent may be a substance existing in a cumyl alcohol solution to be used. For example, when cumyl alcohol is a mixture with cumene as a product, it is possible to use cumene as a substitute of the solvent without adding a solvent in particular.

Though the amount of hydrogen required in the reaction may be equimolar to cumyl alcohol, an excess amount of hydrogen is required because other components which consume hydrogen, are contained in the raw material. Further, the molar ratio of hydrogen to cumyl alcohol is usually from 1 to 10 because the reaction proceeds rapidly by removing water generated to a gas phase through increase of the gas phase part. The ratio is further preferably from 1 to 5. The excess amount of hydrogen remained after the reaction may be recycled after separated from the reaction mixture. The hydrogenolysis temperature is usually 50 to 450° C., preferably 150 to 300° C. In usual, the pressure is advantageously 100 to 10,000 kPa. The hydrolysis can be advantageously carried out using a catalyst in the form of slurry or a fixed bed.

The reaction can be conducted by a batch-wise method, semi-continuous method or continuous method.

When a liquid or gas containing a raw material for reaction is passed through a fixed bed, the catalyst is not contained at all or substantially in a liquid mixture drawn out from the reaction zone.

The above-described process for the production of cumene is suitably applied to a step for producing cumene in propylene oxide production as mentioned below.

Namely, the production of propylene oxide contains the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene in an excess amount; and cumene producing step: a step of producing cumene by hydrogenolysis of cumyl alcohol obtained in the epoxidation step or by hydrogenation subsequent to dehydration of cumyl alcohol and recycling said cumene to the oxidation step.

Each step is explained below.

The oxidation of cumene is usually conducted by auto-oxidation using an oxygen-containing gas such as air or oxygen-concentrated air. This oxidation may be conducted without use of an additive, and an additive such as an alkali may be used. The reaction temperature is usually from 50 to 200° C., and the reaction pressure is usually between atmospheric pressure and 5 MPa. In the oxidation method in which the additive is used, an alkali metal compound such as NaOH or KOH, an alkaline earth metal compound, or alkali metal carbonate such as $Na_2CO_3$ or $NaHCO_3$, ammonia, $(NH_4)_2CO_3$, an alkali metal ammonium carbonate or the like, is used as the alkali reagent. The epoxidation step is preferably conducted in the presence of a catalyst containing titanium-containing silicon oxide from the viewpoint of obtaining propylene oxide under high yield and high selectivity. As these catalysts, so-called Ti-silica catalysts containing Ti chemically bonded to silicon oxide, are preferable. For example, a catalyst prepared by supporting a Ti compound on a silica carrier, a catalyst prepared by combining a Ti compound with silicon oxide by a coprecipitation method or sol gel method, zeolite compounds containing Ti, and the like, can be listed.

Though cumene hydroperoxide used in the epoxidation step, may be a dilute or dense purified material or non-purified material, that from which sodium has been removed, is preferable because sodium is a component accumulated on the catalyst used in the epoxidation step and progress of the accumulation reduces a catalyst activity and may cause to a serious problem such as clogging of the reactor. As a removing method of sodium, there may be used any method of a method of removing the whole or a part of sodium to out of the reaction system of the steps of the present invention by washing, neutralization, extraction or the like, a method of reducing a sodium concentration using an absorbent or the like, and the like.

Considering that there may be a case in which an alkali is used in the oxidation step and a case in which a washing of an alkali is conducted after the oxidation step and separation of water and oil is easy, it is preferable to conduct water-washing before the epoxidation step from the viewpoint of efficient collective removal of sodium.

The epoxidation is conducted by contacting propylene and cumene hydroperoxide with the catalyst. The reaction is carried out in a liquid phase using a solvent. The solvent should be liquid under temperature and pressure during the reaction, and substantially inert to reactants and products. The solvent may be a substance present in a hydroperoxide solution to be used. For example, when cumene hydroperoxide is a mixture with cumene which is a raw material thereof, the cumene can be used as a substitute of a solvent without particularly adding a solvent.

The epoxidation temperature is usually from 0 to 200° C., and preferably from 25 to 200° C. The pressure may be a pressure sufficient to keep the reaction mixture in a liquid condition. In general, the pressure is advantageously from 100 to 10,000 kPa.

The solid catalyst can be advantageously used in the form of a slurry or fixed bed. In the case of a large-scale industrial operation, a fixed bed is preferably used. In addition, the epoxidation can be conducted by a batch-wise method, a semi-continuous method or a continuous method.

When a liquid containing a raw material for reaction is passed through a fixed bed, the catalyst is not contained at all or substantially in a liquid mixture drawn out from the reaction zone. Cumyl alcohol produced in the epoxidation is supplied to the cumene producing step, and cumyl alcohol is usually supplied to the cumene producing step after recovery of propylene oxide and unreacted propylene from the reaction mixture.

In the cumene producing step, cumene is produced by hydrogenolysis or hydrogenation subsequent to dehydration of cumyl alcohol, and in the production, the above-described palladium-based catalyst is used and hydrogen having a CO concentration of 0.1 to 10% by volume is used. Cumene produced is recycled to the oxidation step. Further, cumene may be recycled to the oxidation step after purified by distillation, water-washing or the like.

The present invention is concretely explained in more detail by Examples below.

EXAMPLE

Comparative Example 1 and Examples 1 to 2

Cumyl alcohol is easily converted into α-methyl styrene with activated alumina as a dehydration catalyst. Examples of hydrogenation of α-methyl styrene obtained by dehydration of cumyl alcohol, are shown below.

One hundred grams of a solution composed of 21.5% by weight of α-methyl styrene and 77.9% by weight of cumene, and 0.7 g of a supported-type catalyst, 0.05 wt % Pd/alumina as a hydrogenation catalyst were charged in an autoclave, and reacted in hydrogen containing CO in amounts shown in Table 1 at 200° C. under 1.0 MPa as a gauge pressure for 30 minutes, respectively. α-methyl styrene conversions (conversion of α-methyl styrene into cumene by hydrogenation) and concentrations of isopropyl cyclohexane (i-PrCH)(produced by nuclear-hydrogenation of cumene) are respectively shown in Table 1.

TABLE 1

|  | Comparative Example 1 | Example 1 | Example 2 |
|---|---|---|---|
| CO concentration in Hydrogen (% by volume) | 0 | 1 | 10 |
| α-methyl styrene conversions (% by weight) | >99.9 | 79.2 | 56.2 |
| i-PrCH concentration (ppm by weight) | 285 | <5 | <5 |

Comparative Example 2 and Examples 3 to 5

Examples of nuclear hydrogenation of cumene obtained by hydrogenation of α-methyl styrene.

One hundred grams of cumene and 0.7 g of a supported-type catalyst, 0.05 wt % Pd/alumina as a hydrogenation catalyst were charged in an autoclave, and reacted in hydrogen containing CO in amounts shown in Table 2 at 200' under 1.5 MPa as a gauge pressure for periods shown in Table 2, respectively.

Concentrations of isopropyl cyclohexane (i-PrCH) after the reaction are respectively shown in Table 2.

TABLE 2

|  | Comparative Example 2 | Example 3 | Example 4 | Example 5 |
|---|---|---|---|---|
| CO concentration in Hydrogen (% by volume) | 0 | 0.1 | 1 | 10 |
| Reaction time (minute) | 30 | 30 | 30 | 60 |
| i-PrCH concentration (ppm by weight) | 0.25 | 0.16 | 0.04 | 0.004 |

INDUSTRIAL APPLICABILITY

According to the present invention, there can be provided a process for the production of cumene, which can efficiently convert cumyl alcohol into cumene. In addition, this process can be suitably applied to a cumene producing step of propylene oxide production.

The invention claimed is:

1. A process for producing cumene by subjecting cumyl alcohol to hydrogenolysis or hydrogenation subsequent to dehydration, which comprises using a palladium-based catalyst as a catalyst for the hydrogenolysis or the hydrogenation, and using hydrogen having a carbon monoxide concentration of 0.1 to 10% by volume as hydrogen.

2. The process according to claim 1, wherein the concentration of carbon monoxide is 0.5 to 5% by volume.

3. The process according to claim 1, wherein the cumene is produced by hydrogenolysis of cumyl alcohol.

4. The process according to claim 1, wherein the cumene is produced by dehydrating cumyl alcohol to obtain α-methyl styrene, subsequently hydrogenating α-methyl styrene.

5. A process for producing propylene oxide, which comprises the following steps:
   oxidation step: a step of obtaining cumene hydroperoxide by oxidizing cumene;
   epoxidation step: a step of obtaining propylene oxide and cumyl alcohol by reacting cumene hydroperoxide obtained in the oxidation step with propylene in an excess amount; and
   cumene production step: a step of producing cumene by subjecting cumyl alcohol obtained in the epoxidation step to hydrogenolysis or hydrogenation subsequent to dehydration and recycling said cumene to the oxidation step, and
   which comprises using a palladium-based catalyst as a catalyst for hydrogenolysis or hydrogenation; and using hydrogen having a carbon monoxide concentration of 0.1 to 10% by volume as hydrogen.

6. The process according to claim 5, wherein the concentration of carbon monoxide is 0.5 to 5% by volume.

7. The process according to claim 5, wherein the cumene is produced by hydrogenolysis of cumyl alcohol.

8. The process according to claim 5, wherein the cumene is produced by dehydrating cumyl alcohol to obtain α-methyl styrene, subsequently hydrogenating α-methyl styrene.

* * * * *